United States Patent [19]

Kato et al.

[11] Patent Number: 5,741,681
[45] Date of Patent: Apr. 21, 1998

[54] METHOD FOR PRODUCING L-ASPARTIC ACID

[75] Inventors: Naoki Kato; Yoshiaki Mori; Norioki Mine; Seishi Fujii; Naoyuki Watanabe, all of Yokkaichi, Japan

[73] Assignee: Mitsubishi Chemical Corporation, Tokyo, Japan

[21] Appl. No.: 687,618

[22] PCT Filed: Dec. 8, 1995

[86] PCT No.: PCT/JP95/02526

§ 371 Date: Aug. 8, 1996

§ 102(e) Date: Aug. 8, 1996

[87] PCT Pub. No.: WO96/17950

PCT Pub. Date: Jun. 13, 1996

[30] Foreign Application Priority Data

Dec. 9, 1994 [JP] Japan ................... 6-306217

[51] Int. Cl.$^6$ ............... C12P 13/20; C12P 13/04
[52] U.S. Cl. .................. 435/109; 435/106; 435/233
[58] Field of Search ................ 435/109, 106, 435/233, 829, 832, 849, 874

[56] References Cited

U.S. PATENT DOCUMENTS

| | | | |
|---|---|---|---|
| 391,059 | 7/1888 | Takamura et al. | 435/109 |
| 560,653 | 12/1896 | Sherwin et al. | 435/109 |
| 3,391,059 | 7/1968 | Takamura et al. | 435/109 |
| 4,560,653 | 12/1985 | Sherwin et al. | 435/109 |
| 5,478,919 | 12/1995 | Koskan et al. | 528/363 |
| 5,541,090 | 7/1996 | Sakano et al. | 435/109 |

*Primary Examiner*—Leon B. Lankford, Jr.
*Assistant Examiner*—Christopher R. Tate
*Attorney, Agent, or Firm*—Wenderoth, Lind & Ponack

[57] ABSTRACT

L-aspartic acid is produced by repeating the following respective steps:

(1) a reaction step of producing ammonium L-aspartate from an aqueous solution containing monoammonium maleate in accordance with an isomerization reaction and an enzyme reaction caused by aspartase in the presence of ammonia;

(2) an ammonia-eliminating step of converting substantially all produced ammonium L-aspartate into monoammonium salt by distilling or stripping a reaction solution obtained in the step (1);

(3) a crystallization step of crystallizing L-aspartic acid and producing monoammonium maleate from a solution obtained in the step (2) by adding maleic acid, maleic anhydride or both;

(4) a solid-liquid separation step of separating L-aspartic acid crystals precipitated in the step (3) from a mother liquor containing monoammonium maleate; and (5) a recycle step of supplying the mother liquor containing monoammonium maleate obtained in the step (4) to the step (1) to be used as a raw material for the reaction.

24 Claims, 1 Drawing Sheet

METHOD FOR PRODUCING L-ASPARTIC ACID

BACKGROUND OF THE INVENTION

1. Field of the Invention

The present invention relates to a method for producing L-aspartic acid. In particular, the present invention relates to an industrially advantageous process for producing L-aspartic acid by the aid of an enzymatic action by using maleic acid or maleic anhydride as a raw material.

2. Description of Related Art

L-Aspartic acid is in increasing demand to be used for pharmaceuticals and food additives. Development of new application or use of L-aspartic acid has been also investigated. However, no economically excellent process for industrial production has been established until now. Therefore, it is expected that the demand for L-aspartic acid will greatly increase if mass production is achieved at an inexpensive production cost.

A method for producing L-aspartic acid has been hitherto known, in which L-aspartic acid is obtained in accordance with an enzymatic process by using fumaric acid as a raw material in the presence of ammonia by the aid of the action of aspartase or a microorganism which produces aspartase. However, in the conventional method, sulfuric acid or hydrochloric acid is used to precipitate L-aspartatic acid from the reaction solution which contains ammonium L-aspartate. Therefore, ammonium salt of inorganic acid, which has a low economic value, is by-produced in a large amount, resulting in increase in production cost for L-aspartic acid.

On the other hand, a method has been proposed, in which ammonium L-aspartate obtained by the enzyme reaction is precipitated by adding maleic acid or maleic anhydride, and a mother liquor containing ammonium maleate after recovery of L-aspartic acid crystals is utilized as a raw material (EP 127,940). According to this method, maleic anhydride, which is inexpensive and easily obtainable in a large amount, is used as a raw material. Therefore, this method has a potential to be established as an industrially extremely desirable method if desired L-aspartic acid can be obtained in accordance with a stable continuous operation.

However, in the case of the method described in the patent application, upon crystallization starting from ammonium L-aspartate, it is impossible to increase the recovery of L-aspartic acid crystals unless a large amount of maleic acid is added. Therefore, this method is operated on condition that maleic acid is added in a crystallization step in an amount which exceeds an amount of L-aspartic acid to be crystallized. Accordingly, if a mother liquor containing ammonium maleate after crystallization is recycled, i.e., added to a reaction system and used, the concentration of L-aspartic acid in the system gradually increases. Thus it is impossible to successively perform a stable continuous operation. In sum, it is difficult for the method described above to achieve an industrial continuous operation.

SUMMARY OF THE INVENTION

An object of the present invention is to provide a process for producing L-aspartic acid by using maleic acid as a raw material, in which an aqueous solution of produced ammonium L-aspartate is treated to precipitate by adding constant amount of maleic acid, making it possible to perform a well-balanced and stable continuous operation even when a mother liquor containing ammonium maleate after the precipitation is fully recycled to the reaction system.

As a result of diligent investigations by the present inventors taking the aforementioned circumstances into consideration, it has been found out that ammonium maleate produced by crystallization starting from ammonium L-aspartate is monoammonium salt, while ammonium L-aspartate obtained by using the monoammonium salt as a raw material is a mixture of monoammonium salt and diammonium salt. In sum, in order to precipitate L-aspartic acid after the reaction, maleic acid is required in an amount which is not less than an equimolar amount of ammonium L-aspartate, and monoammonium maleate is produced in an amount corresponding thereto. If the resultant amount of monoammonium maleate is used to produce ammonium L-aspartate, maleic acid is required in an amount which is not less than the amount used in previous time.

Accordingly, it has been conceived in the present invention that an aqueous solution of ammonium L-aspartate after the enzyme reaction is subjected to distillation or stripping so that substantially all ammonium salt is converted into monoammonium salt which is thereafter precipitated by adding maleic acid, thus making it possible to continuously produce L-aspartic acid stably for a long term. Thus the present invention has been completed.

Namely, the gist of the present invention lies in a method for producing L-aspartic acid comprising steps described below.

The method is established as a process for producing L-aspartic acid by using maleic acid, maleic anhydride or both as a raw material, comprising:

(1) a reaction step of producing ammonium L-aspartate from an aqueous solution containing monoammonium maleate in accordance with an isomerization reaction and an enzyme reaction caused by aspartase in the presence of ammonia;

(2) an ammonia-eliminating step of converting substantially all produced ammonium L-aspartate into monoammonium salt by distilling or stripping a reaction solution obtained in the step (1);

(3) a crystallization step of crystallizing L-aspartic acid and producing monoammonium maleate from a solution obtained in the step (2) by adding maleic acid, maleic anhydride or both as an acidic precipitating agent;

(4) a solid-liquid separation step of separating L-aspartic acid crystals deposited in the step (3) from a mother liquor containing monoammonium maleate; and (5) a recycle step of supplying the mother liquor containing monoammonium maleate obtained in the step (4) to the step (1) to be used as a raw material for the reaction.

The present invention will be explained in detail below.

The method of the present invention is established as the process for producing L-aspartic acid by using maleic acid and/or maleic anhydride as a raw material, in which the respective steps (1) to (5) described above are repeatedly carried out. Each of the steps will be explained below.

Step (1):

The step (1) comprises the isomerization reaction (hereinafter referred to as "first reaction", if necessary) for monoammonium maleate, and the enzyme reaction (hereinafter referred to as "second reaction", if necessary) caused by aspartase in the presence of ammonia.

In the step (1), the isomerization reaction described above may be performed prior to the enzyme reaction caused by aspartase (two-step reaction method), or the isomerization reaction and the enzyme reaction cause by aspartase may be simultaneously performed (one-step method).

According to the present invention, L-aspartic acid is produced by repeating the steps described above, in which monoammonium maleate obtained in the step (4) is recycled to the step (1) (step (5)). Upon the start of production, it is also possible to use monoammonium maleate as a raw material. However, maleic acid or maleic anhydride may be used as a starting material in the same manner as performed in conventional production of L-aspartic acid by using maleic acid or maleic anhydride as a raw material. Alternatively, upon the start of production, fumaric acid or ammonium fumarate may be used as a raw material, and the isomerization reaction may be omitted. However, once the production process is started, monoammonium maleate obtained in the step (4) is recycled to the step (1).

The reaction for isomerizing ammonium maleate into ammonium fumarate, and the reaction for converting ammonium fumarate into ammonium L-aspartate by using aspartase are known. In the present invention, these reactions themselves may be carried out in accordance with known methods. The isomerization reaction may be a chemical reaction. However, in the present invention, it is desirable to use an isomerization reaction by using an enzyme.

When the isomerization reaction is performed by using an enzyme, maleate isomerase or a microorganism which produces maleate isomerase is used. The microorganism having a maleate isomerase activity is not specifically limited provided that the microorganism has an ability to isomerize maleic acid and produce fumaric acid, including, for example, microorganisms belonging to the genera Alcaligenes, Pseudomonas, Xanthomonas, and Bacillus. Specifically, the microorganism may be exemplified by *Alcaligenes faecalis*, *Alcaligenes eutrophus*, *Pseudomonas fluorescens*, and *Xanthomonas marutomonasu*. More specifically, the microorganism includes, for example, microbial strains such as *Alcaligenes faecalis* IFO 12669, IFO 13111, and IAM 1473, *Alcaligenes eutrophus* IAM 12305, *Pseudomonas fluorescens* ATCC 23728, and *Xanthomonas marutomonasu* ATCC 13270.

On the other hand, in order to convert ammonium fumarate into ammonium L-aspartate, aspartase or a microorganism which produces aspartase is used so that the conversion reaction is performed on the basis of an enzyme reaction catalyzed by aspartase. This reaction may be performed in accordance with an ordinarily known method. The microorganism which produces aspartase is not specifically limited provided that the microorganism has an ability to produce L-aspartic acid from fumaric acid and ammonia, including, for example, microorganisms belonging to the genera Brevibacterium, Escherichia, Pseudomonas, and Bacillus. Specifically, the microorganism may be exemplified by *Brevibacterium flavum*, *Brevibacterium ammoniagenes*, and *Escherichia coli*. More specifically, the microorganism includes, for example, microbial strains such as *Brevibacterium flavum* MJ-233 (FERM BP-1497) and MJ-233-AB-41 (FERM BP-1498), *Brevibacterium ammoniagenes* ATCC 6872, and *Escherichia coli* ATCC 11303 and ATCC 27325.

The concentration of an aqueous solution of a raw material for the first and second reactions is usually determined by the concentration of an aqueous solution of monoammonium maleate recovered in the crystallization step described later on. Namely, ammonium maleate is converted into ammonium fumarate which is thereafter changed into ammonium aspartate, wherein the concentration of aqueous solutions containing them is approximately constant. The concentration of the aqueous solution of the raw material described above is usually 45 to 700 g/l, preferably 90 to 450 g/l concerning ammonium maleate.

The second reaction is performed in the presence of ammonia. In this procedure, pH in the reaction system is usually 7.0 to 11, preferably 7.5 to 10. The amount of ammonia to be used is 1.05 to 1.7 times in mole, preferably 1.1 to 1.6 times in mole with respect to the amount of monoammonium maleate as the raw material. Ammonia is not essential for the first reaction. However, when the first reaction is performed on the basis of the enzyme reaction, it is preferably performed in the presence of ammonia.

The temperature in the first and second reactions is 10° to 100° C., preferably 20° to 80° C. It is adequate to select a temperature at which the enzyme reaction is efficiently performed.

The reaction procedure for the enzyme reaction usually includes, for example, a method in which an aqueous solution of the raw material is allowed to pass through a packed bed containing immobilized microbial cells, and a method in which an aqueous solution of the raw material is supplied to a reactor containing suspended microbial cells themselves or suspended immobilized microbial cells, while a reaction solution is withdrawn, from which microbial cells are separated by using a separating membrane or a centrifuge and they are returned to the reactor. The same procedure is applicable when the enzyme is used.

When the first and second reactions are simultaneously performed on the basis of the enzyme reactions, microorganisms which produce the respective enzymes are concurrently used to proceed the reactions by selecting a condition suitable for the both reactions. When a microorganism having the both enzymes is used, the microorganism can be used singly. It is not necessarily indispensable to concurrently use two species of microorganisms.

The reaction solution obtained in the second step principally contains ammonium L-aspartate. However, this ammonium salt is a mixture of monoammonium salt and diammonium salt. The ratio of diammonium salt to the total amount of ammonium salt is usually 5 to 70 mole %, preferably 10 to 60 mole %. In some cases, the reaction solution contains unreacted ammonium fumarate and ammonium maleate, however, their contents are desirably controlled to be not more than 2 g/l, preferably not more than 1 g/l. The contents of them can be controlled by optimizing the reaction condition described above.

Step (2):

In the present invention, the reaction solution obtained in the step (1) is subjected to distillation or stripping (the distillation operation or the stripping operation is hereinafter referred to as "ammonia-eliminating operation", if necessary) so that substantially all ammonium L-aspartate obtained in the step (1), preferably not less than 95 mole % thereof, more preferably not less than 97 mole % thereof is converted into monoammonium salt.

Owing to the ammonia-eliminating operation, it is possible to avert the excess amount of maleic acid or maleic anhydride to be used in the crystallization step described later on. Thus a well-balanced industrial process is realized.

The ammonia-eliminating operation may be performed at a normal pressure or a reduced pressure. The operation is performed in a range of 30° to 100° C., preferably 40° to 90° C. If the ammonia-eliminating operation is performed at a low temperature, it is necessary to increase the degree of reduction in pressure, resulting in large restriction for the operation. On the other hand, if the operation is performed at a high temperature, the composition of the solution suffers thermal deterioration, which is not preferred. The temperature condition, especially the upper limit temperature in this step, which inevitably concerns the treatment at the highest temperature among the all steps for constructing the present invention, should be specified as described above from the foregoing viewpoint. When the ammonia-eliminating operation is performed by distillation, a distillation tower is preferably used. The distillation tower may be of a type of an ordinary plate tower or a packed tower.

A residual solution having a molar ratio of ammonia to L-aspartic acid of about 1.0 can be obtained in a still pot by performing the ammonia-eliminating operation for the aqueous solution of ammonium L-aspartate obtained by the enzymatic treatment, in accordance with the method described above.

A vapor separated by the ammonia-eliminating operation contains only ammonia and water. Aqueous ammonia is obtained by recovering the vapor as a liquid by using, for example, a cooling tube. The concentration of the obtained aqueous ammonia is affected, for example, by the temperature and the pressure during the ammonia-eliminating operation, and the temperature during recovery of the vapor.

The aqueous solution obtained after the operation described above is fed to the step (3) described below in order to crystallize L-aspartic acid and recover L-aspartic acid crystals. However, the concentration of ammonium L-aspartate in the aqueous solution to be supplied to the step (3) is usually 50 to 800 g/l, preferably 100 to 500 g/l. If the concentration it too low, the recovery of crystals is low. On the contrary, if the concentration is too high, the concentration of recovered slurry is excessively high, which is not preferred for the operation.

Step (3):

L-Aspartic acid is crystallized by adding, to the solution obtained in the ammonia-eliminating step described above, maleic anhydride and/or maleic acid as an acidic precipitating agent. Maleic acid and/or maleic anhydride to be added may be powder, molten liquid, aqueous solution, or slurry. There is no limitation for the two types of acids to be mixed at an arbitrary ratio.

The molar ratio of (maleic acid+maleic anhydride)/monoammonium L-aspartate is 0.5 to 1.1, preferably 0.6 to 1.0. If the molar ratio is too small, no sufficient recovery is obtained when L-aspartic acid is recovered by solid-liquid separation described later on. As a result, the concentration of aspartic acid in the recycle system becomes high. If the molar ratio is too large, the total number of moles of added maleic acid and maleic anhydride exceeds the number of moles of recovered L-aspartic acid. As a result, when a mother liquor obtained by solid-liquid separation is subjected to isomerization and recycling, an amount of L-aspartic acid corresponding to a difference between the numbers of moles is concentrated. Consequently, it is impossible to stably maintain the process of the recycle system. It is noted that pH of the mother liquor is usually 3 to 6 in the crystallization.

The crystallization temperature is 0° to 90° C., preferably 10° to 80° C., especially preferably 20 to 50° C. If the temperature is too low, obtained crystals are excessively thin. Therefore, the operation for solid-liquid separation becomes troublesome, and the rinsing efficiency is deteriorated as well. Namely, a wet cake obtained by solid-liquid separation contains a large amount of mother liquor (amount of water content), and no sufficient rinsing effect is obtained, resulting in a situation that the purity of crystals is lowered, or if the rinsing amount is increased, the recovery of L-aspartic acid is lowered. On the other hand, if the temperature is too high, the recovery of L-aspartic acid is low, and unpreferable thermal deterioration of maleic acid and ammonium maleate is caused.

The treatment time for the crystallization step is usually about 0.5 to 5 hours.

The crystallization is usually carried out by using a crystallization tank of an agitation tank type. Maleic acid and/or maleic anhydride may be added at any position located on the crystallization tank or on a feeding pipe communicating therewith. The crystallization step is desirably performed in accordance with a continuous system in which the aqueous solution after the ammonia-eliminating described above, maleic acid and/or maleic anhydride are continuously supplied to the crystallization system, while produced slurry is continuously withdrawn. However, a part of the crystallization step may be performed in accordance with an intermittent operation or a batch system.

Step (4):

The obtained slurry is subjected to solid-liquid separation, and obtained crystals are rinsed with water, if necessary. Thus L-aspartic acid crystals are recovered. The obtained crystals can be recovered as a product having a purity of 95% or more by drying the crystals in accordance with an ordinary method.

A mother liquor obtained by the solid-liquid separation contains a major component of monoammonium maleate, however, the mother liquor also contains ammonium L-aspartate in an amount corresponding to its solubility. The mother liquor is recycled to the step (1) described above. Monoammonium maleate contained in the mother liquor is converted by the isomerization reaction into ammonium fumarate which is subjected to the enzyme reaction to be converted into ammonium L-aspartate.

The solid-liquid separation for the slurry is performed in a temperature range of 0° to 80° C., preferably 10° to 50° C., however, the temperature is not specifically limited. If the temperature is too low, the slurry is highly viscous, which is difficult to be handled. If the temperature is too high, the solubility of L-aspartic acid is high, resulting in a lowered recovery. The amount of water to be used for the rinsing operation which is optionally performed is not specifically limited. However, the rinsing operation is performed with water in an amount of not more than five times in weight, preferably not more than three times in weight with respect to a wet cake. If the amount for the rinsing is too small, the rinsing effect is not sufficient, while if it is too large, the recovery of L-aspartic acid is lowered. The temperature of water used for the rinsing is not specifically limited as well.

The separation operation may be performed in accordance with an ordinary method, which is not specifically limited, such as those with a Nutsche funnel and centrifugation.

Step (5):

The mother liquor obtained by the solid-liquid separation principally contains monoammonium maleate, which is an acidic aqueous solution having pH of about 3 to 6. Water is removed from the mother liquor in a concentration step, and ammonia is added thereto, if necessary. An obtained solution is supplied to the step (1).

Other optional steps:

Recovery of ammonia from ammonia-eliminating step:

Aqueous ammonia, which has been separated as a vapor by the ammonia-eliminating operation in the step (2) and recovered by using the cooling tube or the like, is added to the step (5) or the step (1) described above, if necessary. The temperature for supplying ammonia is not specifically limited, however, a good result is obtained when the temperature is 5° to 80° C., preferably 10° to 50° C., considering the reaction temperatures of the respective steps. If the temperature is too high, the vapor pressure of ammonia is high, which is not preferred. No problem arises at all even when aqueous ammonia is supplied at a temperature lower than the reaction temperature.

The method for supplying ammonia to be recycled to the process of the present invention is not specifically limited. No problem arises at all when ammonia is appropriately dispensed to the two reactions of the isomerization reaction and the enzyme reaction in the step (1), or when ammonia is collectively supplied to any one of the two reactions. When the first and second reactions are performed in an identical reactor, ammonia may be supplied to the mother liquor referred to in the step (5).

Partial purge:

It is necessary for the method for producing L-aspartic acid of the present invention to purge some part of recycle system, if necessary, considering accumulation of impurities and reaction by-products.

The position of the purge line is not specifically limited. However, it is preferably located at the still residue aqueous solution stream just after the step (2), because L-aspartic acid is easily recovered as crystals from this purge solution.

The amount of the purge is usually 1 to 20%, preferably 3 to 17% based on a volume of the still residue aqueous solution. If the purge ratio is too low, the effect of preventing impurity accumulation is small and meaningless. If the purge ratio is too high, an apparatus for recovering L-aspartic acid from the purge stream has an volume which is approximately the same as that for the main process, resulting in an economically disadvantageous process. The method for purge may be continuous or intermittent provided that the purge ratio is appropriate.

Usually, L-aspartic acid is recovered as crystals from the purge solution in accordance with a method comprising adding inorganic acid such as sulfuric acid or hydrochloric acid. The amount of inorganic acid to be added is approximately equivalent to that of ammonium aspartate. Namely, it is desirable to add inorganic acid to the purge solution so that an isoelectric point of L-aspartic acid of 2.8 is obtained in order to improve the recovery. In this procedure, salt of inorganic acid is produced as a by-product, however, its amount is small judging from the scale of the entire process.

The technique and the condition for crystallization are the same as those used in the crystallization procedure in the main line described above. For example, the crystallization temperature is 10° to 100° C., preferably 20° to 80° C.

A slurry obtained from the purge solution by the crystallization treatment is also subjected to solid-liquid separation in the same manner as performed in the main line. After that, obtained crystals are rinsed with water, followed by drying to provide a product. Therefore, the crystals after the solid-liquid separation may be mixed, after the rinsing, with crystals obtained in the main line, and they may be subjected to the drying treatment together.

In the present invention, it is preferred that L-malic acid is allowed to co-exist in the crystallization system in an amount of not less than 0.5 g/l, preferably 2.0 to 50 g/l during the crystallization treatment for the purge solution. In sum, in the crystallization of ammonium L-aspartate by the addition of inorganic acid, the deposited crystals are thin plate crystals which have a bad handling property. However, the presence of the specified amount of L-malic acid makes it possible to obtain prismatic crystals having a good handling property.

As for the method for supplying L-malic acid to the crystallization system, L-malic acid may be added to a crystallization tank, however, it is preferred to add a necessary amount of L-malic acid to the aqueous solution of ammonium aspartate. When the aqueous solution of ammonium aspartate is obtained from an aqueous solution of ammonium fumarate or ammonium maleate, L-malic acid may be by-produced depending on the reaction condition. However, the amount of co-existing L-malic acid in the system does not arrive at the aforementioned range when an ordinary crystallization method is used. However, the concentration of L-malic acid in the crystallization system may be controlled by controlling the amount of by-produced L-malic acid or concentrating by-produced L-malic acid.

Almost all ammonium L-aspartate contained in the purge solution can be recovered in accordance with the treatment for the purge solution described above. Moreover, impurities accumulated in the system remain in a mother liquor after crystallization, and they are abandoned. According to the present invention, a well-balanced and stable industrial process can be maintained by connecting the respective steps of the main line comprising the steps (1) to (5), the recovery of ammonia from the ammonia-eliminating step, and the treatment for the purge solution. Thus L-aspartic acid having a constant quality can be produced at a low cost.

The method of the present invention is carried out by sequentially repeating the treatment operations in the respective steps (1) to (5) described above. Each of the steps (1) to (5) may be performed in accordance with a batch process or a continuous process. According to the present invention, for example, when all of the steps are carried out in accordance with the batch process, each of the steps can be operated with an identical treatment amount and under an identical condition even when the reactions are repeatedly performed.

Of course, when all of the steps are carried out in accordance with the continuous process, a well-balanced and stable process is realized.

DETAILED DESCRIPTION OF THE PREFERRED EMBODIMENTS

Figure 1:
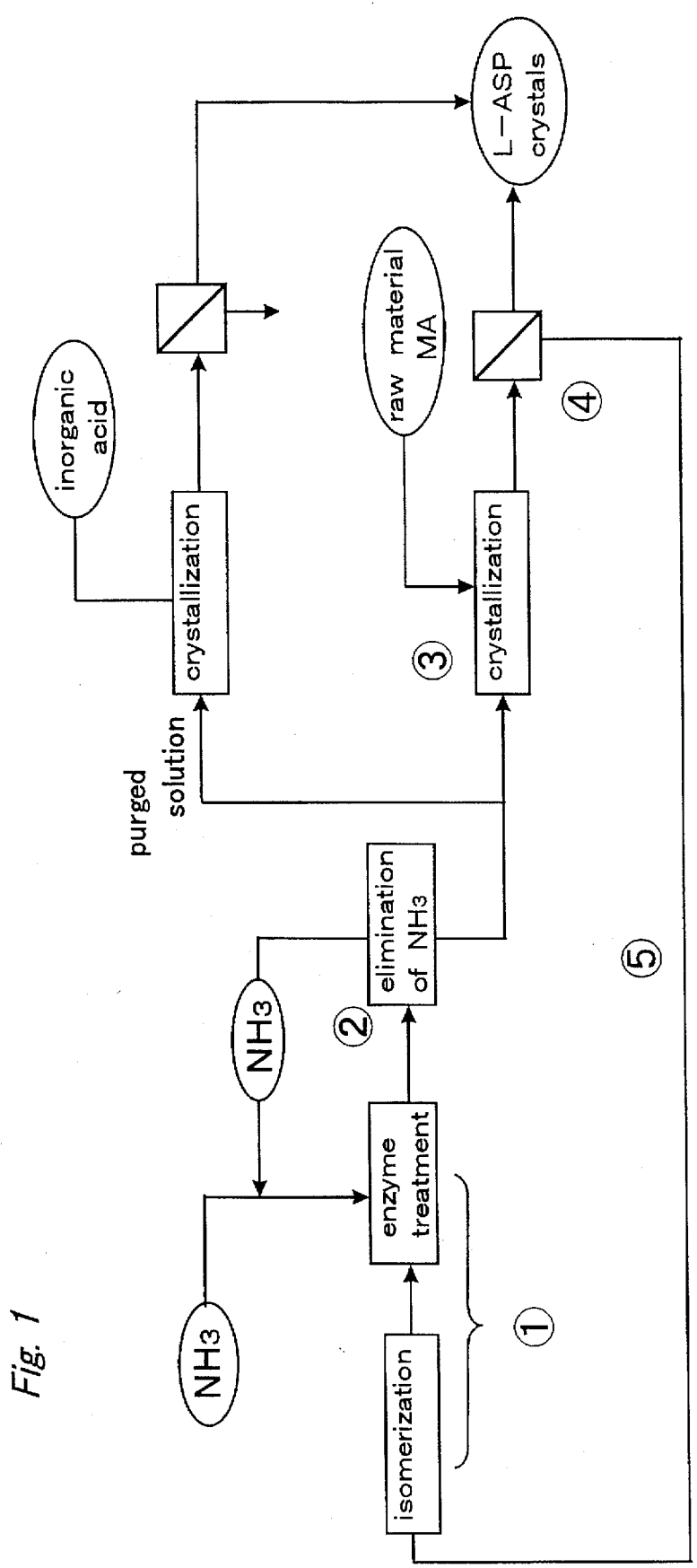
FIG. 1 shows a process diagram illustrating an example of the flow of respective steps according to the present invention.

The present invention will be more specifically explained with reference to Examples. However, the present invention is not limited to the description of Examples provided that the gist is not exceeded.

L-Aspartic acid (hereinafter abbreviated as "ASP"), maleic acid (hereinafter abbreviated as "MA"), and fumaric acid (hereinafter abbreviated as "FA") were analyzed and quantitatively determined by using high-performance liquid chromatography, and the content of ammonia (hereinafter referred to as "NH$_3$") in ASP crystals was analyzed and quantitatively determined by using ion chromatography.

REFERENCE EXAMPLE

Preparation of Aqueous Solution of Ammonium ASP

Concentrated microbial cells (200 g, containing about 50% by weight of wet cells), prepared by using an ultrafiltration membrane (ACV-3050 produced by Asahi Chemical Industry), of *Brevibacterium flavum* MJ-233-AB-41 (FERM BP-1498) having an aspartase activity obtained by an ordinary cultivation method, and concentrated cells (60 g, containing about 50% by weight of wet cells), prepared by using the ultrafiltration membrane (ACV-3050 produced by Asahi Chemical Industry), of *Alcaligenes faecalis* IFO 12669 having a MA isomerase activity obtained by an ordinary cultivation method were added to a raw material solution (aqueous solution containing 150 g of MA, 220 ml of 25% aqueous $NH_3$, added with water to make up a total volume of 1,000 ml, pH 9), and reacted at 30° C. for 24 hours. After completion of the reaction, the microbial cells were removed by using the ultrafiltration membrane, and an obtained filtrate was analyzed. As a result, ASP was 171 g/l (not less than 99% of a theoretical yield), FA was 1.0 g/l, and $NH_3$ was 27.5 g/l. The molar ratio of $NH_3$/ASP was 1.26 (namely, the ratio of diammonium ASP to ammonium ASP was 26%), and pH was 9.

EXAMPLE 1

Production of L-Aspartic Acid (A) The enzyme reaction solution (1 L) obtained by the method described in Reference Example was charged to an round bottom flask (2 L), and ammonia was distilled and separated by using a laboratory evaporator under a condition of 80° C. and 380 mmHg. In order to recover an obtained vapor, a cooling tube was attached to the system so that cooling water containing 50 wt % of ethylene glycol circulated at 0° C. After 15 minutes, the system was returned to a normal pressure, and thus the ammonia-eliminating operation was completed.

A residual solution in the flask had a volume of 825 ml having a composition comprising 207 g/l of ASP and 26.5 g/l of $NH_3$. Distilled water was added to the residual solution to make up a solution having a volume of 850 ml and having a composition comprising 200 g/l of ASP and 25.9 g/l of $NH_3$ (the molar ratio of $NH_3$/ASP was 1.0, i.e., all ammonium salt was monoammonium salt of ASP).

A recovered liquid obtained by using the cooling tube was aqueous $NH_3$ (185 ml) containing 27 g/l of $NH_3$.

(B) The monoammonium ASP aqueous solution (850 ml) obtained in (A) was kept at a temperature of 60° C. in a separable flask (1,000 ml) equipped with the attempered water jacket. The solution was stirred while 119 g of MA (the molar ratio of MA/ASP was 0.80) was added and ASP was precipitated. After the addition of MA, the slurry was kept at a temperature of 60° C. for 30 minutes while continuing agitation. After that, it was cooled to 20° C. over 1 hour, and the temperature was kept for further 30 minutes.

(C) An obtained slurry was subjected to solid-liquid separation by using a Nutsche funnel, which was rinsed with distilled water (400 g), followed by drying at about 60° C. under a reduced pressure. As a result, a white crystalline powder (138.5 g) was obtained.

The obtained solid contained 99.3% by weight of ASP, 0.6% by weight of ammonium MA, and 0.1% by weight of ammonium FA. The recovery of ASP was 80.9%. On the other hand, a mother liquor obtained by the solid-liquid separation had a composition comprising 27.1 g/l of ASP, 98.6 g/l of MA, and 18.6 g/l of ammonia, having pH of about 4.5 and a volume of 1.2 L. Substantially all ammonium MA obtained herein was monoammonium salt, judging from its $NH_3$ balance.

(D) The mother liquor obtained in (C) (1.2 L) was concentrated by removing water at 80° C. under a reduced pressure (300 to 400 mmHg) in accordance with the same method as used in (A). An obtained concentrated solution was added with 185 ml of aqueous $NH_3$ recovered in (A), 80 ml of 25% aqueous $NH_3$, and distilled water to make up a solution having pH of 9.0 and a volume of about 1 L. As a result, its composition was 32.9 g/l of ASP, 0.9 g/l of FA, 119.6 g/l of MA, and 44.6 g/l of $NH_3$.

(E) The solution for the reaction obtained in (D) was subjected to an enzymatic treatment by using microbial cells of *Brevibacterium flavum* and microbial cells of *Alcaligenes faecalis* in accordance with the same method as described in Reference Example. As a result, an obtained composition was 169 g/l of ASP (not less than 99% of a theoretical yield), 1.1 g/l of FA, 0.7 g/l of MA, and 27.5 g/l of $NH_3$. The molar ratio of $NH_3$/ASP was 1.27 (i.e., the ratio of diammonium ASP to ammonium ASP was 27%), and pH was 9.

(F) The same operations as those performed in (A) to (E) described above were repeated three times without changing the conditions. Table 1 shows the yield of the aspartase reaction in each cycle, the yield of L-aspartic acid in crystallization, and the purity of L-aspartic acid in crystals obtained by solid-liquid separation.

TABLE 1

| Times of repetition | Yield of aspartase reaction (%) | Yeild of crystallization (%) | Purity of crystals obtained by solid-liquid separation (%) |
|---|---|---|---|
| 0 | 99 or more | 80.9 | 99.3 |
| 1 | 99 or more | 80.1 | 99.0 |
| 2 | 99 or more | 79.8 | 99.4 |
| 3 | 99 or more | 81.0 | 99.2 |

EXAMPLE 2

Effect of $NH_3$-Eliminating Operation on L-Aspartic Acid Production and Influence of Amount of Added MA in Crystallization Step The same operations as those performed in Example 1 (without repetition) were carried out in the presence or absence of the $NH_3$-eliminating operation (with the $NH_3$-eliminating operation: Experiment Nos. 1 to 4, without the $NH_3$-eliminating operation: Experiment Nos. 5 and 6) while varying the amount of MA added in the crystallization step. Results are shown in Table 2.

TABLE 2

| Experiment number | Molar ratio of $NH_3$/ASP | Molar ratio of added acid in crystallization, MA/ASP | Yield of crystallization (%) |
|---|---|---|---|
| 1 | 1 | 0.4 | 45 |
| 2 | 1 | 0.6 | 64 |
| 3 | 1 | 0.8 | 81 |
| 4 | 1 | 1.0 | 95 |
| 5 | 1.3 | 0.5 | 30 |
| 6 | 1.3 | 0.9 | 70 |

EXAMPLE 3

Recovery of ASP from the Purge Stream

A residual solution in the round-bottom flask obtained by the same operation as that performed in Example 1 (A) was treated in accordance with the same crystallization operation as that performed in Example 1 (B) by using inorganic acid shown in Table 3 in the presence of L-malic acid in an amount shown in Table 3 in the system. Results are shown in Table 3.

TABLE 3

| Experiment number | Molar ratio of NH₃/ASP | Concentration of L-malic acid in system (g/l) | Molar ratio of added acid in crystallization, inorganic acid/ASP |
|---|---|---|---|
| 7 | 1 | 0.1 | 0.5 (H₂SO₄) |
| 8 | 1 | 0.1 | 1.0 (HCl) |
| 9 | 1 | 10.0 | 0.5 (H₂SO₄) |

| Experiment number | Yield of crystallization (%) | Purity of crystals obtained by solid-liquid separation (%) | Form of crystals |
|---|---|---|---|
| 7 | 95 | 99.5 | plate |
| 8 | 96 | 99.1 | plate |
| 9 | 91 | 99.5 | prismatic |

INDUSTRIAL APPLICABILITY

According to the present invention, L-aspartic acid, which is in increasing demand to be used for pharmaceuticals and food additives, can be produced in a large amount at an inexpensive production cost in accordance with the stable continuous operation by using inexpensive maleic anhydride which is easily obtainable in a large amount as a raw material.

What is claimed is:

1. A method for producing L-aspartic acid by using maleic acid, maleic anhydride or both as a raw material, comprising steps of:

(a) subjecting monoammonium maleate in an aqueous solution in the presence of ammonia to an isomerization reaction and an enzyme reaction caused by aspartase to produce ammonium L-aspartate in a reaction solution;

(b) converting substantially all produced ammonium L-aspartate into monoammonium salt by distilling or stripping the reaction solution obtained in the step (a);

(c) adding maleic acid, maleic anhydride or both as an acidic precipitating agent to the solution obtained in the step (b) to precipitate L-aspartic acid crystals and produce monoammonium maleate in a mother liquor;

(d) separating L-aspartic acid crystals precipitated in the step (c) from the mother liquor containing monoammonium maleate; and (e) supplying the separated mother liquor containing monoammonium maleate obtained in the step (d) to the step (a) to be used as a raw material for the reaction.

2. The method according to claim 1, wherein the isomerization reaction in the step (a) is an enzyme reaction caused by maleate isomerase in the presence of ammonia.

3. The method according to claim 2, wherein the isomerization reaction is performed prior to the enzyme reaction caused by aspartase in the step (a).

4. The method according to claim 2, wherein the enzyme reaction caused by maleate isomerase and the enzyme reaction caused by aspartase are simultaneously performed in the step (a).

5. The method according to claim 1, wherein the aqueous solution containing monoammonium maleate to be supplied to the step (a) has a monoammonium maleate concentration of 45 to 700 g/l.

6. The method according to claim 1, wherein ammonium L-aspartate produced in the step (a) contains monoammonium salt and diammonium salt, and a ratio of diammonium salt to all ammonium salt is 10 to 60 mole %.

7. The method according to claim 1, wherein a content of unreacted ammonium fumarate and ammonium maleate in the reaction solution obtained in the step (a) is not more than 2 g/l.

8. The method according to claim 1, wherein the step (b) comprises a distillation treatment performed by using a distillation tower under a reduced pressure at 30° to 100° C.

9. The method according to claim 1, wherein the aqueous solution containing ammonium L-aspartate obtained in the step (b) has an ammonium L-aspartate concentration of 50 to 800 g/l.

10. The method according to claim 3, wherein the aqueous solution containing ammonium L-aspartate obtained in the step (b) has an ammonium L-aspartate concentration of 50 to 800 g/l.

11. The method according to claim 1, wherein the molar ratio of maleic acid, maleic anhydride or both added in the step (c) to the solution obtained in the step (b) to monoammonium L-aspartate is 0.5 to 1.1.

12. The method according to claim 1, wherein crystallization is performed in the step (c) at a temperature of 10° to 80° C.

13. The method according to claim 1, wherein the separated mother liquor in the step (d) has a pH of 3 to 6.

14. The method according to claim 3, wherein the separated mother liquor in the step (d) has a pH of 3 to 6.

15. The method according to claim 1, wherein the L-aspartic acid crystals separated in the step (d) are washed with water followed by drying to obtain crystals having a purity of not less than 95%.

16. The method according to claim 1, wherein 1 to 20% by weight of the solution obtained in the step (b) is purged.

17. The method according to claim 16, wherein L-aspartic acid is crystallized from the solution purged from the step (b) by adding sulfuric acid or hydrochloric acid, and the crystallized L-aspartic acid is recovered.

18. The method according to claim 16, wherein L-aspartic acid is crystallized from the purge solution while allowing 0.5 to 50 g/l of L-malic acid to co-exist in the solution.

19. The method according to claim 17, wherein L-aspartic acid is crystallized from the purge solution while allowing 0.5 to 50 g/l of L-malic acid to co-exist in the solution.

20. The method according to claim 1, wherein ammonia removed from the reaction solution in the step (b) is recycled to the step (a).

21. The method according to claim 3, wherein ammonia removed from the reaction solution in the step (b) is recycled to the step (a).

22. The method according to claim 1, wherein the enzyme reaction caused by aspartase to produce ammonium L-aspartate in the step (a) is performed by using a microorganism selected from the group consisting of those belonging to the genera Brevibacterium, Escherichia, Pseudomonas, and Bacillus.

23. The method according to claim 2, wherein the isomerization reaction in the step (a) is performed by using a microorganism selected from the group consisting of those belonging to the genera Alcaligenes, Pseudomonas, Xanthomonas, and Bacillus.

24. The method according to claim 1, wherein the respective steps (a) to (e) are performed successively and continuously.

* * * * *